United States Patent
Kripp et al.

(12)

(10) Patent No.: US 6,210,660 B1
(45) Date of Patent: *Apr. 3, 2001

(54) COSMETIC PREPARATION CONTAINING ILEX RESIN METHOD FOR OBTAINING ILEX RESIN AND ILEX RESIN WHICH CAN BE OBTAINED BY THIS METHOD

(75) Inventors: Thomas Kripp, Fränkisch-Crumbach; Hiltrud Bormuth, Birkenau-Reifen; Michael Franzke, Rossdorf; Sabine Baecker, Darmstadt; Karl-Heinz Kischka, Darmstadt; Friedel Schröder, Darmstadt, all of (DE)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/312,084

(22) Filed: May 15, 1999

Related U.S. Application Data

(60) Division of application No. 08/930,213, filed on Oct. 6, 1997, now Pat. No. 5,958,395, and a continuation-in-part of application No. PCT/EP97/00797, filed on Jan. 20, 1997.

(30) Foreign Application Priority Data

Feb. 22, 1996 (DE) .............................. 196 06 545

(51) Int. Cl.$^7$ ............................. A61K 35/78; A61K 7/48; A61K 7/06

(52) U.S. Cl. ................................ 424/74; 424/47; 424/43; 424/70.1; 424/70.2; 424/70.6; 424/401; 424/195.1; 514/937

(58) Field of Search .................................. 424/74, 43, 47, 424/70.1, 70.2, 70.6, 401, 195.1, 937

(56) References Cited

U.S. PATENT DOCUMENTS 5,958,395 * 9/1999 Kripp et al. ............................ 424/74

\* cited by examiner

*Primary Examiner*—Diana Dudash
*Assistant Examiner*—Shahnam Sharareh
(74) *Attorney, Agent, or Firm*—Michael J. Striker

(57) ABSTRACT

The subject of the invention is a cosmetic preparation containing Ilex resin which is isolated from leaves of Ilex aquifolium or Ilex paraguariensis, a method for isolating Ilex resin, and the Ilex resin obtained by this method. Skin treatment preparations containing Ilex resin produce a stable protective film on the skin. Hair treatment preparations containing Ilex resin intensify the color, increase luster, contribute to good wet combability, and improve the elasticity of the hair treated with the preparation.

15 Claims, No Drawings

COSMETIC PREPARATION CONTAINING ILEX RESIN METHOD FOR OBTAINING ILEX RESIN AND ILEX RESIN WHICH CAN BE OBTAINED BY THIS METHOD

This application is a Division of Ser. No. 08/930,213 filed Oct. 6, 1997, U.S. Pat. No. 5,958,395 and a continuation-in-part of PCT/EP97/00797 filed Jan. 20, 1999.

The invention relates to a cosmetic preparation containing Ilex resin, which is isolated from leaves of Ilex aquifolium or Ilex paraguariensis, to a method for obtaining this Ilex resin, and to the Ilex resin obtained by this method.

A good appearance is today largely considered an indispensable component of the quality of life. The skin and hairstyle play a particular role here. For changing and designing the hairstyle, the most various preparations and aids are employed.

As a rule, beautiful hair is considered equivalent to healthy hair. The concept of beauty is defined by a number of factors, among which are quite essentially the concepts of "luster" and "depth of color".

Luster, also called gloss, sheen, or shine, is defined physically as the quotient of the oriented component and the diffusely reflected component of the stream of light striking a surface. Hence something's luster is correlated with its surface property, or more specifically its relative roughness. As the roughness increases, the proportion of diffusely reflected light also rises, making for less luster.

The term "depth of color" or "color saturation" is defined as the proportion of pure color to the white component. The white component (in additive color mixing) is composed of the three basic colors, "red", "blue" and "green". For a given color tone of a surface, the roughness of the surface is a decisive factor in its depth of color; the smoother a surface is, the lower the nonspecifically back-scattered white component of the light shone on it, and the more "saturated" the color appears. Wet (or polished) articles therefore generally have a more color-intensive effect than dry ones.

To achieve luster and depth of color, it is accordingly necessary to smooth the applicable surface. This can be achieved, among other ways, by applying a thin, transparent coating with the highest possible index of refraction, which compensates for fine irregularities of the surface.

For hair, this surface coating—applied using suitable recipes—can be made up of various classes of substances. To that end, in the past, above all mineral oils of various fractions, vaseline, various polymers, and recently to an increasing extent silicone oils have been used in hair treatment preparations. The disadvantage of these substances is their poor biodegradability, sometimes a greasy appearance of the hair, and occasional physiological compatability problems.

The object of the invention was therefore to make available a cosmetic preparation with which smoothing of the hair surface and an increase in luster and color depth of the hair can be attained, and which does not have the aforementioned disadvantages.

Along with luster and depth of color, the desired properties of the hair also include in particular elasticity, manageability, and the stability and volume of the hairstyle. The hair is affected mostly negatively in terms of its physical, chemical, and morphological properties by factors of various kinds. The hair is severely stressed and damaged, especially in the region of the ends, by such cosmetic treatments as repeated bleaching, permanent-waving and dyeing, but also by frequent washing with degreasing surfactants, by such climatic factors as humidity and temperature differences, or by the intensive action of sunlight, as well as by such mechanical treatment as brushing, combing, and towel-drying. The hair becomes brittle and loses its luster. The damaged hair becomes electrostatically charged when brushed and combed. The hair surface is roughened, leading to matting and tangling. This all makes the hair extraordinarily difficult to comb and detangle.

Hair conditioning and hair cleaning preparations that improve combability and condition the hair to improve its condition accordingly have considerable significance. In hair conditioning and cleaning preparations, to this end, cationic surfactants, cationic polymers or silicone compounds are employed. They bring about good combability, detangling, and good feel of the hair when wet, but although the criteria when the hair is wet are satisfactory, these factors impair good stylability, elasticity, stability, hold and volume of the hairstyle when the hair is dry.

It was therefore a further object to make available a cosmetic preparation for improving elasticity, manageability, stability and volume of the hairstyle.

Along with preparations for conditioning and cleaning the hair and preparations for changing the color and intensifying the color, preparations for deforming the hair play a particular role. A distinction is made here between preparations for permanent hair deformation, that is, permanent-waving preparations, and preparations for temporarily deforming the hair, which are known as styling products.

Hair styling products or hair strengthening preparations can be applied in the most various forms (lotion, foam, spray, gel, cream). The basis for all hair strengthening preparations is polymers of natural or synthetic origin, which make the essential contribution to strengthening the hair. Since currently available polymers by themselves are not capable of meeting all the demands of a hair strengthening preparation, it is necessary to employ additives, which improve certain properties, in addition to these polymers.

Among the demands made of a hair strengthening preparation is that the preparation should assure a good hold of the hairstyle, along with a pleasant feel, good combability, and good luster. At the same time, the hair should feel as free as possible and have good elasticity. Since additives that improve hair elasticity are quite rare, it was the object of the present invention to make available a cosmetic preparation that improves the elasticity of styling products.

The human skin is exposed to numerous harmful factors. It is stressed by such environmental factors as dryness and cold, for instance. The skin of housewives, doctors and hair stylists, especially, but also of numerous other occupational groups as well, is damaged by repeated washing with wetting or extracting substances or by contact with chemicals. This also includes leaching out by water, and aggressive chemicals such as chlorinated water, saltwater and acidic rain water, UV light, oxidative stress, and drying caused by heat from the sun or a hair dryer, for instance.

To lessen the effect of such stresses, substances that form a protective film can be applied to the skin. They should be hydrophobic, since the harmful factors occur preferentially in conjunction with water; on the other hand, however, it should be possible to wash them out again using soap.

The object of cosmetic preparations for skin treatment is to protect the skin against the above-described harmful environmental factors, to replace the loss of natural skin oils and moisture, and if damage has occurred to promote the restoration of skin functions.

All these objects are attained by using a resin which is isolated from the leaves of Ilex aquifolium (common holly) or Ilex paraguariensis (maté).

The present invention relates to the natural surface coating of the leaves of common hollies (Ilex aquifolium) and mate (Ilex paraguariensis).

The leaves of common hollies are deep green, leathery and glossy in appearance and of considerable sturdiness. In some countries they are used for Christmas decorations indoors. They last for many weeks in heated, dry room air without significantly losing their attractiveness. Clearly, these leaves have a highly effective protective sheath, which not only lends them their deep color and excellent gloss but also protects them against drying out under difficult conditions and against the uncontrolled invasion of oxygen from the air; it can take years before a picked Ilex leaf exhibits signs of wilting and before the chlorophyll, which is otherwise very vulnerable, loses its color or the smooth surface becomes wrinkled.

Surprisingly, it has been discovered that this protective sheath can be isolated and its effect can be employed to meet the needs of cosmetics.

By extraction of Ilex leaves using suitable organic solvents and ensuing removal of the chlorophyll, a raw material can be obtained that is light yellow, hydrophobic, and resinlike in consistency.

It has been demonstrated that an equivalent surface material with very similar properties can be obtained not only from the leaves of the common holly but also from the leaves of the related maté.

The subject of the present invention is therefore a cosmetic preparation containing Ilex resin which is isolated from leaves of Ilex aquifolium or Ilex paraguariensis.

In a further embodiment, along with the Ilex resin, the cosmetic preparation of the invention additionally contains at least one natural or synthetic polymer.

The natural and synthetic polymers are preferably selected from the groups of strengthening and thickening polymers. The polymers can be used in amounts from 0.1 to 20 weight % and in either dissolved form or in the form of a dispersion.

A preferred embodiment is a cosmetic preparation for strengthening the hair, which is characterized in that it contains (A) from 0.001 to 10 weight %, preferably from 0.01 to 3.5 weight %, Ilex resin (B) from 0.01 to 25 weight %, preferably from 0.1 to 20 weight %, of at least one natural or synthetic polymer (C) from 30 to 99.89 weight % of a suitable organic, aqueous-organic or aqueous solvent, and optionally additives for further improving the product profile.

A further subject of the invention is a cosmetic preparation for skin treatment containing Ilex resin which is isolated from leaves of Ilex aquifolium or Ilex paraguariensis. For the skin treatment preparation according to the invention, it can be demonstrated that a more-stable protective film is formed, compared with a standard preparation.

A partial replacement of paraffins with Ilex resin in emulsions also brings about an improvement in shelf life at elevated temperatures.

A further subject of the invention is a method for obtaining Ilex resin from the leaves of Ilex aguifolium or Ilex paraguariensis by solvent extraction in a manner known per se using a semipolar or apolar, water-free organic solvent or using supercritical carbon dioxide. In a preferred embodiment, (a) the leaves are hot-extracted at least twice using acetic acid ethyl ester and hot-filtered, and the filtrate is condensed until dry, and then (b) the residue is placed in a nonpolar organic solvent, fuller's earth is added to the warm solvent, the mixture is heated to boiling and hot-filtered, and the filtrate is condensed until dry.

The extractions in method step (a) can be repeated multiple times to improve the yield. Continuous extraction is also suitable. In continuous extraction, the medium must have a temperature of at least 60° C. in the extraction product. Suitable solvents for extraction step (a) are distillable organic solvents, as free of water as possible, having at least two carbon atoms, or supercritical $CO_2$. Semipolar to apolar solvents are preferred. In the cleaning step (b), chlorophyll, triterpenes, caffeine and glycosides are removed.

The Ilex resin is chemically a mixture of free fatty acids, hydrocarbons and fatty acid esters, is translucent orange-yellow in color, and of tough, resinous consistency.

If the cosmetic preparation according to the invention is used for hair treatment, then it contains from 0.001 to 10 weight % Ilex resin, preferably between 0.1 and 5 weight %. This preparation can then either be rinsed out or left in the hair.

The cosmetic preparation according to the invention, if used for hair treatment, has a pH of between 2 and 8 and preferably between 4 and 7.

For use as a hair treatment according to the present invention, the cosmetic preparation can additionally contain all the usual ingredients used in hair treatment preparations, in particular anionic, cationic, amphoteric or non ionic surfactants, emulsifiers, foam synergists; foam stabilizers; sequestering agents, natural ingredients; pigments; perfume oils in a quantity of from 0.1 to 5.0 weight %; opacifiers, such as ethylene glycol distearate, in a quantity from approximately 0.5 to 5.0 weight %; pearlescent agents, such as a mixture of fatty acid monoalkylolamide and ethylene glycol distearate, in a quantity from approximately 1.0 to 10.0 weight %; thickening agents, such as coconut fatty acid diethanolamide or hydroxyalkylcellulose, in a quantity from 0.5 to 10.0 weight %; physiologically compatible organic or inorganic acids and buffer substances, such as citric acid, tartaric acid, lactic acid, formic acid, glyoxylic acid, sodium citrate or sodium phosphate in a quantity from 0.1 to 1.0 weight %; and hair and product dyes, such as sodium fluorescein salt, yellow ZN3 (C. I. 47055), in a quantity from 0.1 to 1.0 weight %; other hair conditioning additives, such as amino acids, proteins, herb extracts, betaines, vitamins, carbohydrates and derivatives thereof, urea, etheric oils, fatty acid esters, fatty alcohols, fatty acid glycerides, ethoxylated or propoxylated saturated fatty alcohols; natural, modified natural, or synthetic polymers, such as shellac, cationic, anionic or nonionic cellulose derivatives, chitosan, cationic chitin or chitosan derivatives, or polymers of acrylic acid derivatives; conditioning substances such as lanolin derivatives, cholesterol and pantothenic acid, in a quantity from 0.1 to 10 weight percent; also physiologically compatible inorganic salts, such as sodium chloride and sodium sulfate; also moisteners; sunscreen agents; antioxidants; complexing agents; antidandruff agents; conditioning lipids of mineral or biogenic origin, such as cosmetic oils, fats, terpenes, steroids and waxes, as well as preservatives, to the extent that such additives appear useful and expedient and are compatible with the ingredients with the preparation according to the invention.

The cosmetic preparation according to the invention for hair treatment preferably contains Ilex resin, surfactants, emulsifiers, and organic and inorganic acids or buffer substances.

If the cosmetic preparation according to the invention is used to clean skin or hair, then it contains anionic, amphoteric or nonionic surfactants in a quantity from 0.01 to 40 weight %, preferably 0.1 to 25 weight % and water in a quantity from 50 to 99 weight %, and the pH is between 3 and 8, preferably between 4 and 7. The aforementioned surfactants can also be used in mixtures.

Examples of anionic surfactants that can be used are acyl glutamates, sarcosinates, acyl peptides, salts of carboxylic acids, taurates, carboxylic acid esters and their salts, carboxylic acid ethers and their salts, phosphoric acid esters and their salts, sulfonic acids and their salts, alkyl ether sulfates, alkyl sulfates, and isethionates; alkaline or alkaline earth salts of lauryl ether sulfates are especially preferred.

Examples of amphoteric surfactants that can be used are N-alkylbetaines, N-alkylaminobetaines, fatty acid amidoalkylbetaines, fatty acid amidoalkylsulfobetaines, and carboxyl derivatives of imidazol. Coconut fatty acid amidopropylbetaine is preferably used, which is sold for instance by Goldschmidt under the trade name Tego® Betain L5045.

Examples of nonionic surfactants that can be used are alkylpolyglucosides, alkenolamides, monoglycerides, ethoxylated alcohols, and polyglycerine fatty acid esters. Preferably, alkylpolyglucoside of the kind sold by Henkel under the tradename Plantaren® 2000 CS/UP or Plantaren® 818 UP or that sold by by Seppic under the tradename Oramix® NS10 is used.

An especially preferred version can contain cationic polymers in a quantity from 0.01 to 8 weight %, preferably 0.05 to 5 weight %, such as a vinylpyrrolidone/dimethylaminoethylmethacrylate copolymer quaternized with dimethyl sulfate and sold for instance by GAF under the trade name Gafquat® 755N, or cationic cellulose, as sold by Union Carbide under the trade name Ucare® Polymer JR.

If the cosmetic preparation of the invention is used for hair conditioning and is prepared in the form of an emulsion or dispersion, then in addition to the Ilex resin it contains lipids, such as fatty alcohols, paraffin oils, fatty acid glycerine esters, silicone compounds, or higher hydrocarbons in a quantity from 0.01 to 30 weight %, as well as emulsifiers. As the lipid, straight-chained fatty alcohols with n carbon atoms in a quantity from 0.05 to 18 weight %, where n represents the number 8 to 22, or a mixture of such fatty alcohols in which n indicates the average number of carbon atoms, are especially preferred. Suitable fatty alcohols or fatty alcohol mixtures are sold for instance by Henkel under the trade name Lanette® 14, 16, 18 and 22 and Lanette® 0.

As the higher hydrocarbon, isododecane in a quantity from 0.05 to 15 weight % is preferably used.

As emulsifiers, cationic, anionic, amphoteric or nonionic surfactants are used, preferably in a quantity from 0.03 to 8 weight %. Examples of suitable cationic surfactants as emulsifiers are alkyldimethylbenzylammonium chlorides or bromides, cetyltrimethylammonium chloride or bromide, tetradecyltrimethylammonium chloride or bromide, dialkyldimethylammonium chlorides or bromides, alkylpyridinium salts such as lauryl- or cetylpyridinium chloride, alkylamidoethyltrimethylammonium ethosulfates, quaterary esters such as dipalmitoylethyldimethylammonium chloride, which is sold for instance by Akzo under the trade name Armosoft® VGH-70, and compounds of cationic nature such as amine oxides, for instance alkylmethylamine oxides or alkylaminoethyldimethylamine oxides.

As cationic surfactants, the preparations preferably contain cetyltrimethylammonium chloride and/or distearyldimethylammonium chloride in a quantity from 0.03 to 8 weight %.

Examples of suitable anionic surfactants as emulsifiers are acyl glutamates, sarcosinates, acyl peptides, salts of carboxylic acids, taurates, carboxylic acid esters and their salts, carboxylic acid ethers and their salts, phosphoric acid esters and their salts, sulfonic acids and their salts, alkyl ether sulfates, alkyl sulfates, and isethionates. As the anionic surfactant, the preparations preferably contain sodium cetyl stearyl sulfate in a quantity from 0.03 to 8 weight %.

Examples of suitable amphoteric surfactants as emulsifiers or coemulsifiers are N-alkylbetaines, N-alkylaminobetaines, fatty acid amidoalkylbetaines, fatty acid amidoalkylsulfobetaines, carboxyl derivatives of imidazol, and capryloiminodipropionate, which is sold for instance by Akzo under the trade name Ampholak® YJH-40. As amphoteric surfactants, the preparations preferably contain cocoamido-propylbetaine and/or stearyldimethylglycine in a quantity from 0.03 to 8 weight %. Examples of suitable nonionic surfactants as emulsifiers or coemulsifiers are alkylpolyglucosides, alkenolamides, monoglycerides, ethoxylated alcohols, and polyglycerine fatty acid esters, lecithin and cholesterol. The preparations preferably contain alkylpolyglucosides, which are sold for instance by Henkel under the trade names Plantaren® 1200 CS/UP, Plantaren® 2000 CS/UP or Plantaren® 818 UP, in a quantity from 0.03 to 8 weight %.

The cosmetic preparation according to the invention for hair conditioning preferably has a water content of 75 to 99 weight %, can contain alcohol in quantity from 0.1 to 25 weight %, and has a pH of 2 to 8, preferably 2.5 to 7. Alcohols that can be considered are in particular the lower alcohols usually used for cosmetic purposes, having from 2 to 4 carbon atoms, such as ethanol or isopropanol.

If the cosmetic preparation of the invention is used for strengthening the hair, then it is preferably in the form of an alcohol, aqueous or aqueous-alcohol solution. Examples of suitable organic solvents are straight-chained or branched alcohols with a chain length from $C_1$ to $C_5$ with up to three hydroxyl groups. Also suitable are straight-chained or branched hydrocarbons with a chain length from $C_1$ to $C_8$. Other solvents that can be named in addition are glycol ether and water. Examples of preferred solvents that can be named are alcohols with a chain length up to $C_4$, hydrocarbons with a chain length up to $C_7$, and water in combination with suitable solubilizers. The concentration of these solvents may be between 30 and 99.89 weight %.

For the cosmetic preparation according to the invention for strengthening the hair, the following classes of substances can be named as optional ingredients:

Anionic, nonionic, cationic and amphoteric surfactants and emulsifiers; volatile and nonvolatile silicone compounds, solubilizers, antifoaming agents, combability promoters, perfume oils, vegetable extracts, proteins and protein hydrolisates, native oils, higher hydrocarbons such as paraffins, neutralizers, preservatives, UV absorbers, antioxidants, dyes, pigments, and propellant gases.

The cosmetic preparation according to the invention for strengthening or conditioning the hair can be sprayed on, using a propellant or a mechanically operated sprayer, or dispensed as foam using a foam generating device.

If the cosmetic preparation of the invention is sprayed with the aid of a propellant, then it preferably contains from 3 to 75 weight % of the propellant and is packaged in a pressurized container.

Examples of suitable propellants are lower alkanes, such as n-butane, i-butane and propane or mixtures thereof, or dimethyl ether and fluorinated hydrocarbons, such as F 152 (1,1-difluoroethane) or F 134 (tetrafluoroethane), as well as propellants that are in gaseous form at the pressures in question, such as $N_2$, $N_2O$ and $CO_2$, as well as mixtures of the aforementioned propellants.

Mechanical sprayers or foam generating devices are understood to be devices that make it possible to spray or foam up a liquid without using a propellant. Examples of a suitable mechanical sprayer that can be used are a spray pump or an elastic container provided with a spray valve, into which the cosmetic preparation of the invention is introduced under pressure, causing the elastic container to expand, and from which the preparation is dispensed continuously, by the contraction of the elastic container, when the spray valve is opened. As a suitable mechanical foam generating device, the attachment described in European Patent Disclosure EP-B 0 0460 154, with a foam generator on a flexible container.

If the cosmetic preparation of the invention is used for hair conditioning, then it is employed as follows:

After the hair is washed and dried with a hand towel, from 5 to 30 g of the preparation is distributed, depending on the fullness of the hair, and left to act for approximately 3 to 15 minutes. The preparation is then rinsed out and the hair combed through and optionally shaped into the hairstyle and dried. A preferred embodiment of the preparation according to the invention can be left in the hair; that is, it is not rinsed out and thus saves one step for the user.

If the cosmetic preparation of the invention is used for skin treatment, then it contains between 0.001 and 50 weight % of Ilex resin, preferably between 0.1 and 10 weight %. It may be in the form of solutions, suspensions, pastes, gels or emulsions, but preferably in the form of oil in water or water in oil emulsions, and can be packaged preferably as a face lotion, skin cream, body lotion, face pack, or face mask.

The cosmetic preparation of the invention for skin treatment can additionally contain all those ingredients that are typically used in skin treatment preparations, in particular an ionic, nonionic, cationic, amphoteric or amphionic surfactants, such as ethoxylated fatty alcohols with from 12 to 18 carbon atoms, for instance with up to 40 Mols of ethylene oxide per Mol of fatty alcohol, ethoxylated lauryl, cetyl or stearyl alcohol, alkylbetaines, alkylaminobetaines, alkylsulfobetaines and fatty acid alkylamidobetaines in a quantity from 0.01 to 5.0 weight %; sequestering agents; emulsifiers; natural substances, such as vitamins, preferably vitamins F and B6, D-pantothenol, amino acids such as betaine, cysteine, alanine, valine, or tyrosine, proteins, carbohydrates and derivatives thereof or vegetable extracts, pigments, perfume oils, and etheric oils, in a quantity from 0.5 to 5.0 weight %; opacifiers, such as ethylene glycol distearate, in a quantity from approximately 0.5 to 5.0 weight %; moisteners, such as glycerine, polyols, hyaluronic acid and urea, in a quantity from 0.05 to 20 weight % and preferably from 0.1 to 10 weight %; pearlescent agents, such as a mixture of fatty acid monoalkylolamide and ethylene glycol distearate, in a quantity from approximately 1.0 to 10.0 weight %; thickening agents, such as coconut fatty acid diethanolamide or hydroxyalkylcellulose, in a quantity from 0.1 to 1.0 weight %; organic or inorganic acids or buffer substances, such as sodium citrate or sodium phosphate in a quantity from 0.1 to 1.0 weight %; as well as dyes, such as sodium fluorescein salt, yellow ZN3 (C. I. 47055), in a quantity from 0.1 to 1.0 weight %; as well as hair conditioning additives, such as conditioning lipids of mineral or biogenic origin, fatty acid esters, fatty alcohols, fatty acid glycerides, terpenes, steroids; natural, modified natural, or synthetic polymers, such as cationic, anionic or nonionic cellulose derivatives, chitosan, cationic chitin or chitosan derivatives, conditioning agents such as lanolin derivatives, cholesterol, allantoin, α-bisabolol, azulene and pantothenic acid, in a quantity from 0.1 to 10 weight %; also physiologically compatible inorganic salts, such as sodium chloride and sodium sulfate; also sunscreen agents; antioxidants; complexing agents; titanium dioxide; cosmetic oils and waxes, and preservatives, to the extent that such additives appear useful and expedient and are compatible with the ingredients of the preparation used.

The pH of the cosmetic preparation for skin treatment according to the invention is preferably 4 to 7 and may be adjusted with physiologically compatible organic or inorganic acids or bases, for instance with benzoic acid, citric acid, formic acid or acetic acid, sorbic acid, sodium hydroxide, ammonia, or mono- or triethanolamine. The cosmetic preparation for skin treatment according to the invention may be water-free or can contain up to 99.5 weight % of water. The cosmetic preparation for skin treatment according to the invention preferably has a water content of 50 to 80 weight %.

As a chemically invariable natural substance, Ilex resin, despite being highly hydrophobic, is biodegradable, and as an ingredient in a widely sold food and by chemical analysis it can be classified as toxicologically unobjectionable.

In a hair gloss preparation, the use of Ilex resin intensifies the color compared with hair treated with a comparison recipe. In addition, the Ilex resin product leaves behind greater luster.

The hair treated with the hair conditioning and/or cleaning preparations according to the invention also has very good wet combability and an appealing feel. The hair has pronounced luster, as well as elasticity and tensile strength. The hairstyle can be achieved easily and is distinguished by good hold and volume.

Hair that has been treated with the hair treatment preparation according to the invention, which contains Ilex resin in addition to natural or synthetic polymers, is distinguished by improved elasticity, more luster and surprisingly by improved strength as well.

Emulsions that contain the Ilex resin of the invention have greater emulsion stability, at temperatures of around 40° C., than emulsions lacking any Ilex resin content.

The following examples are intended to describe the subject of the invention in more detail.

EXAMPLES

Example 1

Obtaining Ilex resin 1 kg of maé tea (Ilex paraguariensis) or 1 kg of common holly leaves (Ilex aquifolium) are extracted in reflux for 2 h, using 3.2 l of acetic acid ethyl ester. The extract is then hot-filtered at a temperature of at least 60° C. The residue is mixed with 2.8 l of acetic acid ethyl ester and stirred in reflux for 1 h. The result is then hot-filtered. The reextraction can be repeated multiple times. The yield then increases by approximately 0.3% per reextraction step.

In order to remove chlorophyll, triterpenes, caffeine and glycosides, the combined filtrates from the various extractions are condensed until dry. The dark-green residue is placed in approximately 1 l of hexane or petroleum ether (boiling range 60 to 80° C.) and heated. A residue of polar components remains undissolved. While stirring and still before the boiling temperature is reached, 35 g of fuller's earth (Tonsil Supreme FF made by Süd-Chemie, Munich, Germany) are added. Further heating, while stirring, is now done for a further 15 minutes in reflux. The fuller's earth is then allowed to settle for approximately another 10 minutes. The result is then hot-filtered. The filtrate is condensed until dry (vacuum≦100 mbar, water bath approximately 70° C.).

Yield: approximately 24 g of orange-yellow, translucent, tough Ilex resin.

Analysis of the Ilex resin shows that it contains saturated and unsaturated, long-chained hydrocarbons, free fatty acids, and saturated and unsaturated fatty acid esters. Chromatograms and physical-chemical properties indicate an extensive match between the resin obtained from maté tea and that obtained from common holly leaves.

Example 2

Skin cream to protect against leaching

| | |
|---|---|
| 10.0 g | Ilex resin in accordance with Example 1 |
| 10.0 g | liquid paraffin |
| 15.0 g | lanolin alcohol extract (Amerchol L101 made by Amerchol, Edison, New Jersey, USA) |
| 10.0 g | lanolin, anhydr. |
| 8.0 g | glycerine monodistearate |
| 0.3 g | p-hydroxy benzoic acid methyl ester/ p-hydroxy benzoic acid propyl ester 70:30 |
| 0.2 g | perfume oil |
| 46.5 g | water |
| 100.0 g | |

Example 3

Skin protection cream (water in oil emulsion)

| | A | B | C | D | E |
|---|---|---|---|---|---|
| Ilex resin per Example 1 | 10.0 g | 0.10 g | 20.0 g | 40.0 g | 50.0 g |
| Lanolin alcohol extract (Amerchol L101 made by Amerchol, Edison, New Jersey, USA) | 15.0 g | 15.00 g | 15.0 g | 15.0 g | 15.0 g |
| Liquid paraffin | 10.0 g | 19.90 g | — | — | — |
| Lanolin anhydr. | 10.0 g | 10.00 g | 10.0 g | 10.0 g | 10.0 g |
| Glycerine monodistearate | 8.0 g | 8.00 g | 8.0 g | 8.0 g | 8.0 g |
| Water | 47.0 g | 47.00 g | 47.0 g | 27.0 g | 17.0 g |
| | 100.0 g | 100.00 g | 100.0 g | 100.0 g | 100.0 g |

The pH of the emulsion is between 6 and 7.

Example 4

Hand cream (oil in water emulsion)

| | A | B | C | D | E |
|---|---|---|---|---|---|
| Ilex resin per Example 1 | 10.0 g | 0.10 g | 20.0 g | 40.0 g | 50.0 g |
| Glycerine (86%) | 15.0 g | 15.00 g | 15.0 g | 15.0 g | 15.0 g |
| Liquid paraffin | — | 9.90 g | — | — | — |
| Cetyl/stearyl isononanoate | 5.0 g | 5.00 g | 5.0 g | 5.0 g | 5.0 g |
| Glycerine monodistearate | 4.0 g | 4.00 g | 4.0 g | 4.0 g | 4.0 g |
| Water | 66.0 g | 66.00 g | 56.0 g | 36.0 g | 26.00 g |
| | 100.0 g | 100.00 g | 100.0 g | 100.0 g | 100.00 g |

The pH of the hand cream is between 6 and 7.

Example 5

Skin Protection Gel

| | A | B | C | D |
|---|---|---|---|---|
| Ilex resin per Example 1 | 0.10 g | 0.50 g | 1.0 g | 10.0 g |
| Glycerine (86%) | 30.00 g | 30.00 g | 30.0 g | 30.0 g |
| Cellulose ether | 4.00 g | 4.00 g | 4.0 g | 4.0 g |
| Hydr. recinus oil, ethoxylated with 45 Mol of ethylene oxide | 0.20 g | 1.00 g | 2.0 g | 20.0 g |
| Water | 65.70 g | 64.50 g | 63.0 g | 36.0 g |
| | 100.00 g | 100.00 g | 100.0 g | 100.0 g |

The pH of the skin protection gel is between 5 and 6.

Example 6

Microemulsion for improving the luster and color depth of hair

| | |
|---|---|
| 7.25 g | Ilex resin per Example 1 |
| 10.00 g | liquid paraffin |
| 9.00 g | tetraoxyethylene lauryl ether |
| 3.75 g | dioxyethylene lauryl ether |
| 1.75 g | cetyltrimethylammonium chloride |
| 0.20 g | perfume oil |
| 0.20 g | citric acid |
| 0.15 g | sorbic acid |
| 67.80 g | water |
| 100.0 | |

Example 7

Clear gloss cream for the hair

| | A | B | C | D |
|---|---|---|---|---|
| Ilex resin per Example 1 | 0.25 g | 1.00 g | 2.00 g | 3.00 g |
| Liquid paraffin | 17.00 g | 16.25 g | 15.25 g | 14.25 g |
| Tetraoxyethylene lauryl ether | 9.00 g | 9.00 g | 9.00 g | 9.00 g |
| Dioxyethylene lauryl ether | 3.75 g | 3.75 g | 3.75 g | 3.75 g |
| Cetyltrimethylammonium chloride | 1.75 g | 1.75 g | 1.75 g | 1.75 g |
| Citric acid | 0.20 g | 0.20 g | 0.20 g | 0.20 g |
| Sorbic acid | 0.15 g | 0.15 g | 0.15 g | 0.15 g |
| Water | 67.90 g | 67.90 g | 67.90 g | 67.90 g |
| | 100.00 g | 100.00 g | 100.0 g | 100.0 g |

| | E | F | G |
|---|---|---|---|
| Ilex resin per Example 1 | 4.00 g | 5.00 g | 7.25 g |

-continued

| | | | |
|---|---|---|---|
| Liquid paraffin | 13.25 g | 12.25 g | 10.00 g |
| Tetraoxyethylene lauryl ether | 9.00 g | 9.00 g | 9.00 g |
| Dioxyethylene lauryl ether | 3.75 g | 3.75 g | 3.75 g |
| Cetyltrimethylammonium chloride | 1.75 g | 1.75 g | 1.75 g |
| Citric acid | 0.20 g | 0.20 g | 0.20 g |
| Sorbic acid | 0.15 g | 0.15 g | 0.15 g |
| Water | 67.90 g | 67.90 g | 67.90 g |
| | 100.00 g | 100.00 g | 100.0 g |

The pH of the luster cream is between 3 and 4.

Example 8

Foam strengthener

| | |
|---|---|
| 0.1 g | Ilex resin per Example 1 |
| 10.0 g | ethanol |
| 8.0 g | propane/butane 5.0 bar |
| 0.8 g | chitosan |
| 0.2 g | formic acid |
| 0.2 g | methylvinylimidazolium chloride/vinyl-pyrrolidone copolymer |
| 0.2 g | hydrogenated recinus oil, ethoxylated with 40 Mol of ethylene oxide |
| 0.2 g | herb extract (Extrapone 5 Spezial made by Dragoco, Germany) |
| 0.1 g | tetraoxyethylene lauryl ether |
| 0.1 g | perfume |
| 80.1 g | water |
| 100.0 g | |

Example 9

Hair spray

| | |
|---|---|
| 0.5 g | Ilex resin per Example 1 |
| 2.5 g | acrylate/acrylamide copolymer |
| 0.2 g | 2-amino-2-methyl propanol |
| 0.1 g | perfume |
| 46.7 g | ethanol |
| 50.0 g | butane 1.5 bar |
| 100.0 g | |

Example 10

Pump spray

| | |
|---|---|
| 0.34 g | Ilex resin per Example 1 |
| 10.00 g | vinylpyrrolidone/vinyl acetate copolymer, 50% in ethanol |
| 0.30 g | shellac |
| 0.15 g | perfume |
| 0.01 g | 2-amino-2-methylpropanol |
| 5.00 g | water |
| 84.20 g | ethanol |
| 100.00 g | |

Example 11

Liquid strengthener with elasticity component

| | |
|---|---|
| 0.5 g | Ilex resin per Example 1 |
| 7.0 g | isodecane |
| 2.5 g | vinyl acetate/crotonic acid copolymer |
| 0.2 g | perfume |
| 0.1 g | cetyltrimethylammonium bromide |
| 0.1 g | glycerine |
| 44.6 g | water |
| 45.0 g | ethanol |
| 100.0 g | |

Example 12

Hair cleaning preparation with conditioning action

| | |
|---|---|
| 0.6 g | Ilex resin per Example 1 |
| 9.6 g | sodium lauryl ether sulfate |
| 3.5 g | sodium chloride |
| 2.0 g | polyethylene glycol-(3)distearate |
| 1.5 g | coconut fatty acid amidopropylbetaine |
| 0.4 g | perfume oil |
| 0.3 g | vinylpyrrolidone/dimethylaminoethyl-methacrylate copolymer |
| 82.1 g | water |
| 100.0 g | |

Example 13

Hair conditioning preparation to be rinsed out

| | |
|---|---|
| 1.5 g | Ilex resin per Example 1 |
| 2.5 g | cetyl stearyl alcohol |
| 0.4 g | cetyltrimethylammonium chloride |
| 0.4 g | perfume oil |
| 0.3 g | citric acid |
| 94.9 g | water |
| 100.0 g | |

Example 14

Hair conditioning preparation not to be rinsed out

| | |
|---|---|
| 0.7 g | Ilex resin per Example 1 |
| 0.6 g | cetyl stearyl alcohol |
| 0.4 g | vinylpyrrolidone/dimethylaminoethyl-methacrylate copolymer |
| 0.2 g | cetyltrimethylammonium chloride |
| 0.2 g | citric acid |
| 0.2 g | perfume oil |
| 97.7 g | water |
| 100.0 g | |

Example 15

Sprayable hair conditioner not to be rinsed out

| | |
|---|---|
| 0.20 g | Ilex resin per Example 1 |
| 8.00 g | ethanol |
| 0.45 g | hydrogenated tallow trimethylammonium chloride |
| 0.20 g | mixture of glyceryl stearate and cetyl stearyl polyethylene glycol-(20) (Teginacid(R) made by Th. Goldschmidt, Germany) |
| 0.15 g | cetyl stearyl alcohol |
| 0.13 g | N-stearylbetaine |
| 0.10 g | perfume oil |
| 90.77 g | water |
| 100.00 g | |

Example 16

Hair conditioning foam to be rinsed out

| | |
|---|---|
| 1.1 g | Ilex resin per Example 1 |
| 3.0 g | cetyl stearyl alcohol |
| 1.2 g | lauryl polyglucose, 50% (Plantaren(R) 1200 CS/UP made by Henkel KGaA, Germany) |
| 1.2 g | cetyltrimethylammonium chloride |
| 0.4 g | perfume oil |
| 93.1 g | water |
| 100.0 g | |

94.0 g of the above hair conditioner are placed along with 6 g of a mixture of 75 weight % n-butane, 20 weight % i-butane and 5 weight % propane in a suitable aerosol container. The hair conditioner of the invention is dispensed from the container in the form of a foam.

Example 17

Hair conditioner foam that remains in the hair

| | |
|---|---|
| 0.7 g | Ilex resin per Example 1 |
| 4.5 g | isododecane |
| 1.0 g | diquaternary polydimethylsiloxane (Abil(R) Quat 3272 made by Th. Goldschmidt, Germany) |
| 0.5 g | polyvinylpyrrolidone |
| 0.4 g | α-hydro-omega-hydroxypolyoxydimethylsilylene (CTFA: dimethiconol), 13%, in cyclic dimethyl polysiloxane (CTFA: cyclomethicone) (Dow Corning Q2 1401 Fluid made by Dow Corning Europe, Belgium) |
| 0.2 g | cetyltrimethylammonium chloride |
| 0.2 g | perfume oil |
| 0.1 g | vinylpyrrolidone/dimethylaminoethyl-methacrylate copolymer |
| 97.4 g | water |
| 100.0 g | |

96.0 g of the above hair conditioner are placed along with 4 g of a mixture of 50 weight % propane, 40 weight % n-butane and 10 weight % dimethyl ether in a suitable aerosol container. The hair conditioner of the invention is dispensed by spraying from the container in the form of a foam.

Example 18

Hair conditioner to be rinsed out

| | |
|---|---|
| 1.40 g | Ilex resin per Example 1 |
| 5.20 g | cetyl stearyl alcohol |
| 2.70 g | wool fat |
| 2.00 g | glycerine monodistearate with potassium distearate |
| 1.17 g | sodium cetyl stearyl sulfate |
| 0.80 g | wool wax |
| 0.50 g | mixture of lanolin and lanolin alcohol (Aquaphil(R) K, sold by Deutsche Lanolin Gesellschaft, Germany) |
| 0.30 g | perfume oil |
| 0.20 g | cholesterol |
| 85.73 g | water |
| 100.00 g | |

Example 19

Comparison test for skin protection action

| | |
|---|---|
| 20.0 g | liquid paraffin |
| 15.0 g | lanolin alcohol extract (Amerchol L101 made by Amerchol, Edison, New Jersey, USA) |
| 10.0 g | lanolin, anhydr. |
| 8.0 g | glycerine monodistearate |
| 0.3 g | p-hydroxy benzoic acid methyl ester/ p-hydroxy benzoic acid propyl ester 70:30 |
| 0.2 g | perfume oil |
| 46.5 g | water |
| 100.0 g | |

The water-repellent action on the skin and the resistance to being rinsed off is increased for the skin cream of Example 2 according to the invention, compared with the comparison cream of Example 19.

Example 20

Comparison test for hair conditioning action

| | |
|---|---|
| 17.25 g | liquid paraffin |
| 9.00 g | tetraoxyethylene lauryl ether |
| 3.75 g | dioxyethylene lauryl ether |
| 1.75 g | cetyltrimethylammonium chloride |
| 0.20 g | perfume oil |
| 0.20 g | citric acid |
| 0.15 g | sorbic acid |
| 67.80 g | water |
| 100.0 g | |

Hair treated with the microemulsion of Example 6, compared with hair treated with the emulsion of Example 20, had more luster and a greater depth of color.

All the percentages given in this application represent weight percents.

What is claimed is:

1. A cosmetic composition containing:
   from 0.001 to 50 percent by weight of an Ilex resin; and
   from 0.01 to 40% by weight of at least one anionic, amphoteric or non-ionic surfactant;
   wherein said Ilex resin is made by a method comprising extracting leaves of Ilex aquifolium or Ilex paraguariensis with a semipolar or apolar, water-free organic solvent, either continuously or in successive multiple extraction steps.

2. A cosmetic composition containing:

from 0.001 to 50 percent by weight of an Ilex resin;

from 0.01 to 30% by weight of at least one hair-conditioning active ingredient selected from the group consisting of lipids, paraffin oils and silicone compounds; and from 0.03 to 8% by weight of at least one emulsifiers selected from the group consisting of cationic surfactants, anionic surfactants, amphoteric surfactants and nonionic surfactants;

wherein said Ilex resin is made by a method comprising extracting leaves of Ilex aquifolium or Ilex paraguariensis with a semipolar or apolar, water-free organic solvent, either continuously or in successive multiple extraction steps.

3. A cosmetic composition containing from 0.001 to 10 percent by weight of an Ilex resin;

from 0.01 to 25% by weight of at least one natural or synthetic polymer; and from 30 to 99.89% by weight of an organic, aqueous-organic or aqueous solvent;

wherein said Ilex resin is made by a method comprising extracting leaves of Ilex aquifolium or Ilex paraguariensis with a semipolar or apolar, water-free organic solvent, either continuously or in successive multiple extraction steps.

4. A method of promoting hair gloss comprising the step of applying a hair gloss preparation comprising an effective amount of an Ilex resin;

wherein said Ilex resin is made by a method comprising extracting leaves of Ilex aquifolium or Ilex paraguariensis with a semipolar or apolar, water-free organic solvent, either continuously or in successive multiple extraction steps.

5. A method of stabilizing an oil-in-water emulsion or a water-in-oil emulsion to provide a longer emulsion lifetime, said method comprising including in the emulsion an effective amount of an Ilex resin;

wherein said Ilex resin is made by a method comprising extracting leaves of Ilex aquifolium or Ilex paraguariensis with a semipolar or apolar, water-free organic solvent, either continuously or in successive multiple extraction steps.

6. A method of obtaining an Ilex resin, said method comprising the step of extracting leaves of Ilex aquifolium or Ilex paraguariensis with supercritical carbon dioxide.

7. The method as defined in claim 6, further comprising repeating the extracting multiple times to improve yield of the Ilex resin.

8. The method as defined in claim 6, wherein the extracting is continuous at a temperature of at least 60° C.

9. The method as defined in claim 6, further comprising placing said Ilex resin obtained by the extracting in a nonpolar organic solvent, then adding Fuller's earth to the nonpolar organic solvent to form a mixture, heating the mixture to boiling and hot-filtering and condensing the filtrate until dry, whereby a purified portion of said Ilex resin is obtained.

10. An Ilex resin obtained by a method comprising the step of extracting leaves of Ilex aquifolium or Ilex paraguariensis with supercritical carbon dioxide, either continuously or in successive multiple extraction steps.

11. A cosmetic composition containing:

from 0.001 to 50 percent by weight of an Ilex resin; and from 0.01 to 40% by weight of at least one anionic, amphoteric or non-ionic surfactant;

wherein said Ilex resin is made by a method comprising extracting leaves of hex aquifolium or hex paraguariensis with supercritical carbon dioxide, either continuously or in successive multiple extraction steps.

12. A cosmetic composition containing:

from 0.001 to 50 percent by weight of an Ilex resin;

from 0.01 to 30% by weight of at least one hair-conditioning active ingredient selected from the group consisting of lipids, paraffin oils and silicone compounds; and from 0.03 to 8% by weight of at least one emulsifiers selected from the group consisting of cationic surfactants, anionic surfactants, amphoteric surfactants and nonionic surfactants;

wherein said Ilex resin is made by a method comprising extracting leaves of Ilex aquifolium or Ilex paraguariensis with supercritical carbon dioxide, either continuously or in successive multiple extraction steps.

13. A cosmetic composition containing from 0.001 to 10 percent by weight of an Ilex resin;

from 0.01 to 25% by weight of at least one natural or synthetic polymer; and from 30 to 99.89% by weight of an organic, aqueous-organic or aqueous solvent;

wherein said Ilex resin is made by a method comprising extracting leaves of Ilex aquifolium or Hex paraguariensis with supercritical carbon dioxide, either continuously or in successive multiple extraction steps.

14. A method of promoting hair gloss comprising the step of applying a hair gloss preparation comprising an effective amount of an Ilex resin;

wherein said Ilex resin is made by a method comprising extracting leaves of Ilex aquifolium or Ilex paraguariensis with supercritical carbon dioxide, either continuously or in successive multiple extraction steps.

15. A method of stabilizing an oil-in-water emulsion or a water-in-oil emulsion to provide a longer emulsion lifetime, said method comprising including in the emulsion an effective amount of an Ilex resin;

wherein said Ilex resin is made by a method comprising extracting leaves of Ilex aquifolium or Ilex paraguariensis with supercritical carbon dioxide, either continuously or in successive multiple extraction steps.

* * * * *